United States Patent [19]

Shelnutt

[11] Patent Number: 4,917,784
[45] Date of Patent: Apr. 17, 1990

[54] PROCESS FOR LIGHT-DRIVEN HYDROCARBON OXIDATION AT AMBIENT TEMPERATURES

[75] Inventor: John A. Shelnutt, Tijeras, N. Mex.

[73] Assignee: The United States of America as represented by the United States Department of Energy, Washington, D.C.

[21] Appl. No.: 412,736

[22] Filed: Sep. 26, 1989

[51] Int. Cl.[4] .............................................. B01J 19/08
[52] U.S. Cl. .......................... 204/157.6; 204/157.61; 204/157.9; 204/157.93
[58] Field of Search ............. 204/157.6, 157.61, 157.9, 204/157.93

[56] References Cited

U.S. PATENT DOCUMENTS 4,427,511  1/1984  Wohlgeniuth ................. 204/157.6
4,568,435  2/1986  Shelnutt ....................... 204/157.52

Primary Examiner—John F. Niebling
Assistant Examiner—Ben C. Hsing
Attorney, Agent, or Firm—Armand McMillan; James H. Chafin; William R. Moser

[57] ABSTRACT

A photochemical reaction for the oxidation of hydrocarbons uses molecular oxygen as the oxidant. A reductive photoredox cycle that uses a tin(IV)- or antimony(V)-porphyrin photosensitizer generates the reducing equivalents required to activate oxygen. This artificial photosynthesis system drives a catalytic cycle, which mimics the cytochrome $P_{450}$ reaction, to oxidize hydrocarbons. An iron(III)- or manganese(III)-porphyrin is used as the hydrocarbon-oxidation catalyst. Methylviologen can be used as a redox relay molecule to provide for electron-transfer from the reduced photosensitizer to the Fe or Mn porphyrin. The system is long-lived and may be used in photo-initiated spectroscopic studies of the reaction to determine reaction rates and intermediates.

20 Claims, 1 Drawing Sheet

PROCESS FOR LIGHT-DRIVEN HYDROCARBON OXIDATION AT AMBIENT TEMPERATURES

BACKGROUND OF THE INVENTION

1. Field of the Invention

The present invention relates to a process for the oxidation of hydrocarbons that uses molecular oxygen as the oxidant and more particularly to a catalytic cycle, driven by an artificial photosynthesis system, which mimics the cytochrome $P_{450}$ reaction to oxidize alkanes and olefins. The Government has rights in this invention pursuant to Contract No. DE-AC04-76DP00789 awarded by the U.S. Department of Energy to AT&T Technologies, Inc.

2. Description of Related Art

Cytochrome $P_{450}$ is a typical mono-oxygenase, inserting one oxygen atom of $O_2$ into a substrate molecule and using the other to form HO. Any catalyst which mimics cytochrome $P_{450}$ is a biomimetic oxidation catalyst; it mimics the biological oxidation reactions of Cytochrome $P_{450}$. Visible light has been used to activate $O_2$ for room-temperature conversion of alkanes to alcohols. One of the drawback of a biomimetic approach to oxidation of nycrocarbons ls that a strong reductant is required at two stages in the catalytic cycle using an Fe porphyrin. When molecular oxygen is used as the oxidant, as is the case for cytochrome $P_{450}$, the reductant reduces iron from $Fe^{III}$ or $Fe^{II}$ so that $O_2$ can bind. Then, another reductant molecule is expended to break the ) O-O bond to provide the reactive Fe-O intermediate. Strong reductants such as Zn, $NaBH_4$, and $H_2$ have been used for this purpose. These reductants are valuable in themselves and must be replenished to sustain the hydrocarbon-oxidation reaction.

Previously, a system which mimics biological photosynthesis has been disclosed in U.S. Pat. No. 4,568,435 to Shelnutt. This artificial photosynthesis system uses a tin porphyrin as a light absorbing pigment to produce reducing equivalents.

Previously, a great variety of alkane and olefin oxidation systems that mimic biological oxidation of hydrocarbons by cytochrome $P_{450}$ have been reported. Most use an iron, manganese, or ruthenium porphyrin as the analog of the heme (iron porphyrin) functional group of the enzyme. Ortiz de Montellano, P.R., ed."Cytochrome P-450, Structure, Mechanism, and Biochemistry" (Plenum: New York) 1986; Guengerich, F.P.; Macdonald, T.L., Acc. Chem. Res. 1984, 17,9; Groves, J.T.; Nemo, T.E. et al., J. Am. Chem. Soc. 1979, 101,1032. In the great majority of these chemistries a single oxygen atom donor, such as iodosylbenzene or hypochlorite, is used as the oxidant rather than molecular oxygen. However, Karasevich et al., Institute of Chemical Physics, U.S.S.R. Academy of Sciences, J. Chem. Soc., Chem. Commun. 1987, 731-732 discloses that cytochrome $P_{450}$ activation of dioxygen on iron porphyrin as a catalytic center can be accomplished using of Zn(Hg) as a reducing agent, methylviologen as a mediator and acetic anhydride as an acylating agent. Nevertheless, the Russian hydrocarbon-oxidation system employed a non-newable reductant and, hence, the yield was low.

SUMMARY OF THE INVENTION

Accordingly, it is an object of the present invention to provide a more efficient and longer lived chemical system for the oxidation of hydrocarbons.

Another object of the present invention is to improve product yield in a catalytic cycle, which mimics the cytochrome $P_{450}$ reaction, to oxidize hydrocarbons.

A further object of the invention is to provide a method for oxidizing hydrocarbons which may be turned on and off using light.

Yet another object of the invention is to provide a method for oxidizing hydrocarbons which can be operated over long periods without adding system components other than light and $O_2$ for the process.

A still further object of the invention is to provide a method for oxidizing hydrocarbons that can be initiated using pulse lasers.

Yet a further object of the invention is to provide a method for oxidizing hydrocarbons the course of which can be followed using time resolved Raman and absorption spectroscopies.

Further still, another object of the invention is to provide a method for determining reaction rates and for identifying intermediate species in the reaction cycles for the purpose of optimizing the reaction.

Yet still further, another object of the invention is to provide a solvent in which both the catalytic and the reductive photoredox cycles are functional.

These and other objects are accomplished by the present invention which provides:

A method for oxidizing hydrocarbons in a catalytic cycle that mimics photosynthesis which comprises the steps of:

providing a solution comprising a metalloporphyrin photosensitizer that generates reducing equivalents for activating oxygen, a biomimetic hydrocarbon-oxidation catalyst, molecular oxygen as the oxidant, a hydrocarbon substrate molecule, a sacrificial electron donor and a solvent; and irradiating said solution with light in the presence of molecular oxygen.

Preferably, the metalloporphyrin photosensitizer of the reaction solution comprises a tin (IV)- or an antimony (V)- porphyrin present in a concentration which ranges from about $1 \times 10^{-8}$ to $1 \times 10^{-3}$ M.

The hydrocarbon-oxidation catalyst of the reaction solution is preferably Fe tetra(pentafluoro-phenyl)porphyrin chloride or another sterically unhindered iron or manganese porphyrin which is present in a concentration which preferably ranges from about $1 \times 10^{-8}$ to $1-10^{-3}$ M.

Desirable hydrocarbon substrate molecules useful in the reaction solution of the present invention include hexane, cyclohexane, hexenes of any type, butane, butene, ethane, ethylene, methane or aromatics such as p-xylene. The substrate should be present in a concentration which ranges from about $3 \times 10^{-3}$ M to 0.03M.

Suitable sacrificial electron donors useful in the reaction solution of the present invention include triethanolamine, triethylamine, ethylenediaminetetraacetic acid, ascorbate or mercaptoethanol. The sacrificial electron donor should be present in a concentration which ranges from about $1 \times 10^{-3}$ M to 0.3M.

The solvent of the reaction solution of the present invention is preferably an organic solvent such as acetonitrile.

An electron relay molecule optionally may be used in the reaction solution of the present invention and is preferably heptylviologen, benzyl viologen or methyl viologen. The electron relay molecule is preferably present in a concentration which ranges from about $1 \times 10^{-5}$ M to $3 \times 10^{-3}$ M.

The acylating agent preferably ranges in concentration from $1 \times 10^{-5}$M to $3 \times 10^{-3}$M so as to at least equal the concentrations of the iron porphyrin and preferably double the concentration of the iron porphyrin.

The environment in which the hydrocarbon oxidation takes place preferably includes light having a wavelength within the visible spectrum and, more preferably, ranging from about 380 nm to 700 nm.

The environment in which the hydrocarbon oxidation takes place preferably includes air or molecular oxygen to be used as the oxidant. A temperature range at which the hydrocarbon oxidation occurs is between about 20° C. and 35° C.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
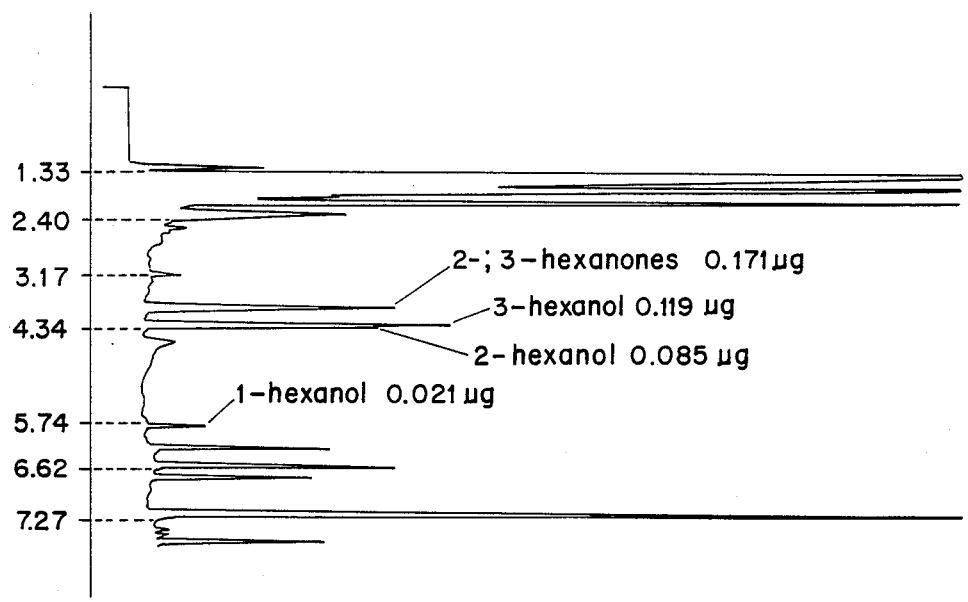
FIG. 1 is a chart showing a gas chromatogram giving the yields of 1-,2-, and 3-hexanol and 2- and 3-hexanone produced in Example 1 below.

Described below is a photochemically driven system for oxidation of alkanes and olefins in accordance with the present invention. The system is illustrated in Scheme 1.

Scheme 1. Benzyl and methyl viologens may also serve as relay molecules in place of heptylviogen ($HV^{2+}$) In the example of a preferred embodiment illustrated in Scheme 1, two molecules of reduced $HV^{2+}$ ($HV^+$) or of the porphyrih anion are required in the biomimetic $P_{450}$ cycle. It is also possible that SnP radical anion can directly transfer an electron to FeP, in which case the relay molecule is not required.

The Fe(III)-porphyrin catalyst after being reduced by the Sn porphyrin $\pi$-anion or the reduced viologen, binds $O_2$. Subsequent reduction of the Fe(II)-$O_1$-porphyrin complex results in a high oxidation-state intermediate. The intermediate is capable of inserting a single O-atom into a C-H bond of the hydrocarbon substrate to give the alcohol. Further oxidation is sometimes observed resulting in ketones, aldehydes, and carboxylic acids. The oxidation reaction results in oxidized hydrocarbon and the original Fe(III)-porphyrin catalyst. This reaction cycle mimics the biological reaction carried out by the enzyme cyctochrome $P_{450}$.

An acylating agent such as acetic or benzoic anhydride aids the catalytic reaction by promoting the splitting of the O-O bond of the bound oxygen molecule and, therefore, the formation of the active Fe-O porphyrin intermediate.

An organic solvent, such as acetonitrile, suffices as a solvent for the reaction mixture herein described.

The desired concentrations of iron or manganese porphyrin and tin(IV)- or antimony(V)-protoporphyrin should not be so low as to cripple the reaction. The iron or manganese porphyrins used in the present invention are sterically unhindered so as to allow for oxidation of many different types of alkane and olefin substrates.

The photosensitizers employed, namely the protopor-

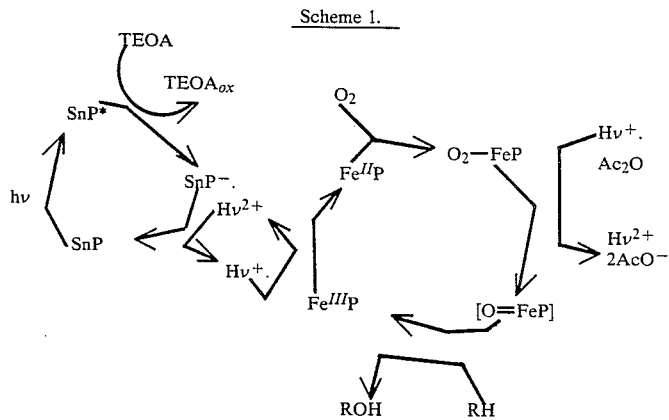

Scheme 1.

The cycle on the left is the photoredox chemistry that produces the reductant, in this case the reduced form of heptylviologen ($HV^{2+}$) In the cycle, tin(IV)- or antimony(V)-porphyrin(SnP), in its triplet excited state, is reduced by a sacrificial electron donor such as triethanolamine (TEOA), triethylamine, ethylenediaminetetraacetic acid, ascorbate or mercaptoethanol.

The resulting long-lived $\pi$-radical anion of the porphyrin has a redox potential low enough to reduce $HV^{2+}$, which is detected by its characteristic red absorption at 602 nm. After reduction of the relay (or the FeP directly as noted below), the photosensitizer (SnP) returns to the resting redox state.

Heptylviologen may optionally act as an electron relay molecule between the photocycle and the cytochrome-$P_{450}$-like chemical cycle on the right side of phyrins, typically show a tendency to dimerize and form $\pi$-$\pi$ complexes and dimers at concentrations approaching 0.01M ($1 \times 10^{-2}$M), and these $\pi$-complexes are photochemically inactive. However, the Sn- and Sb-protoporphyrins, typical of metals with strongly bonded axial ligands cannot form these complexes and dimers. Accordingly, desired concentrations for both iron or manganese porphyrins and tin(IV) or antimony(V)-protoporphyrins range from $1 \times 10^{-8}$M to $1 \times 10^{-2}$M the higher concentrations provide better collection of radiant energy.

Reduced viologen ($HV^+$ in Scheme 1) reaches a steady-state concentration at about $1 \times 10^{-4}$M, as measured by McLendon and Miller. Since viologen may also mediate acylation of the oxidized Fe-porphyrin the minimum viologen concentration should be $1 \times 10^{-4}$M The concentration should range from about $1 \times 10^{-4}$M to 1M.

The electron donor and hydrocarbon substrate constituents should not be the limiting reagents in this reaction. The steady-state concentration for ethylenediaminetetraacetic acid is 0.27M. For triethylamine, the steady-state concentration can range from $1 \times 10^{-3}$M to 0.1M. Consequently, concentrations for the electron donor should range from $2 \times 10^{-3}$M in more dilute (catalyst) reactions to 2M. Corresponding concentrations of hydrocarbon substrates should range from $1 \times 10^{-3}$M to 1M, in order that the substrate molecules can accept the number of electron equivalents supplied by the electron donors.

EXAMPLE 1

The production of the oxidized hydrocarbon is monitored by gas chromatography (GC). FIG. 1 shows the GC results for a typical run. The yields correspond to catalyst turnover of 0.5, 1.8 and 2.6 respectively for the alcohols. The batch reactor containing: (1) 0.75 ml acetonitrile, (2) 0.1 ml hexane. (3) 0.15 ml TEOA, (4) 0.36 mg $SnCl_2$, Protoporphyrin, (5) 0.24 mg FeTF$_5$PPCL, and (6) 2.53 mg benzoic anhydride is stirred at a moderate rate in the presence of air. The solution is irradiated for 3 hours with a tungsten-halide lamp and projector at room temperature.

FIG. 1 shows the gas chromatogram giving the yields of 1-, 2-, and 3-hex-anol- and the combined 2- and 3-hexanone yield. The yields correspond to catalyst turnover numbers of 0.5, 1.8, 2.6, and 3.8, respectively. In the absence of the electron relay $HV^{2+}$, the reduction of the Fe-porphyrin catalyst occurs by direct interaction with the Sn-porphyrin anion, a biomimetic process similar to electron transport between Fe porphyrins in cytochromes of the electron-transport chain. This photochemical system also carries out hydroxylation of hexane in the absence of benzoic anhydride.

EXAMPLE 2

A photochemical reaction like that illustrated in Scheme 1 is carried out in acetonitrile under an $O_2$ or air atmosphere. In a typical reaction, 0.24 μmol of Fe(III) tetra(pentafluoro-phenyl)porphyrin (FeTF$_5$PP) chloride, 0.45 μmol of Sn(IV)-protoporphyrin IX (SnProtoP) dichloride, 1.1 mmol of TEOA, 1.4 μmol of heptylviologen (N,N'-diheptyl-4,4'-dipyridinium dichloride), and 11 μmol of benzoic (or acetic) anhydride, are added to 1 ml of acetonitrile. Hexane (4.7 mmol) is added as a substrate. The samples, contained in a 1-cm path length cuvette, are irradiated with a tungsten lamp for 1-6 hours. Light of wavelengths less than 380 nm is filtered to insure that photosensitization of the reaction occurs only due to visible absorption by the porphyrin. Hexanol and hexanone products are quantified at the end of the run by gas chromatography. Table 1 gives typical yields and hexanol to hexanone product ratios for typical runs and control experiments. The system produces stable yields of oxidized hydrocarbons for more than 6 hours.

In the absence of $O_2$, light, photosensitizer, or triethanolamine, there is no significant yield of oxidized hexane. However, in the absence of the catalyst FeTF$_5$PP, photosensitized production of hexanols and hexanones is observed in an average ratio of 2.3. In the presence of the P$_{450}$ catalyst, a generally higher overall yield of products is observed when illumination and other conditions are identical; however, a lower average hexanol to hexanone ratio of 1.3 is observed.

TABLE 1

Photo-oxidation of hexane in acetonitrile by air.

| Catalyst | Photo-sensitizer | Reductant | -ol/-one | Yield[a] (turnovers/hr) |
|---|---|---|---|---|
| FeTF$_5$PP | SnProtoP | TEOA | 1.3[b] | 4.3 |
| — | SnProtoP | TEOA | 2.3[b] | 1.7 |
| — | H$_2$ProtoP | TEOA | 2.7 | 0.6 |
| — | SbProtoP | TEOA | 2.2 | 1.4 |
| FeTF$_5$PP | SbProtoP | TEOA | 1.0 | 0.8 |
| — | — | TEOA | — | 0.0 |
| — | SnProtoP | — | — | 0.0 |
| FeTF$_5$PP | — | TEOA | 0.8 | 0.2 |
| MnTPP | SnProtoP | TEOA | 0.9 | 0.2 |

[a]Yield is for selected run
[b]hexanol/hexanone value is average for all (~20) runs with turnovers >1.

It is apparent that more than one oxygen activation pathway exists. The excited triplet state of tin porphyrin is known to be quenched in the presence of $O_2$, suggesting a possible direct mechanism of $O_2$ activation by the photosensitizer. Reactions of both singlet $O_2$ and superoxide anion have also been examined under the above reaction conditions. Chemically produced superoxide ($KO_2$-18-crown-6) is not reactive under our experimental conditions. On the other hand, singlet oxygen, produced by irradiation of free base porphyrin, is reactive in the presence of tertiary amines and gives about the same hexanol to hexanone ratio (2.7, see Table 1) as is observed in the presence of the SnP photosensitizer. Sn-, Sb-, and free base prophyrins all have triplet lifetimes of 10 ms or longer, and form singlet $O_2$ by intermolecular triplet-triplet annihilation. In fact, the photophysical parameters and singlet oxygen sensitizing properties of SnProtoP are similar to metal-free porphyrins. The similarity of photosensitizing characteristics of Sn-, Sb-, and H$_2$ pophyrins explains the similarity of their properties in the FeP-free reaction (Table 1). However, only the Sn and Sb porphyrins form the stable anions capable of driving the Fe-porphyrin catalyzed reaction.

EXAMPLE 3

In the presence of the iron-porphyrin, the alcohol/ketone product ratio is modified (-ol/-one ≈ 1) indicating that a competing reaction comes into play. If the FeP catalyzed reaction is to account for the low product ratio, then this reaction necessarily must give a lower hexanol to hexanone ratio. Table 2 shows the yield and product ratio for the dark reaction of hexane and $O_2$catalyzed by FeTF$_5$PP. The reaction is run for 2 hours.

TABLE 2

Oxidation of hexane in acetonitrile by $O_2$ using Zn/Hg amalgam.

| Catalyst | Addend(s) | -ol/-one | Tot. Yield (turnovers) |
|---|---|---|---|
| FeTF$_5$PP | Ac$_2$O, MV | 0.2[a] | 1.0[a] |
| — | Ac$_2$O, MV | 4.4[b] | 0.0 |
| H$_2$TF$_5$PP | Ac$_2$O, MV | 1.2 | 0.1 |
| FeTF$_5$PP | Na$_2$SO$_4$-dried Ac$_2$O, MV | 0.1 | 0.1 |
| FeTF$_5$PP | Ac$_2$O, MV, 5% H$_2$O | 0.3 | 0.5 |
| FeTF$_5$PP | Ac$_2$O, MV | 0.2 | 0.8 |
| FeTF$_5$PP | CH$_3$COOH, ±MV | 0.6 | 1.1 |
| FeTF$_5$PP | Ac$_2$O, CH$_3$COOH, MV | 0.4 | 0.3 |
| FeTF$_5$PP | H$_2$O, CH$_3$COOH, MV | 0.7 | 0.8 |
| MnTPP | Ac$_2$O, MV | 1.3[b] | 0.0 |
| MnTPP | Ac$_2$O, MV, Im | 1.1 | 0.5 |

[a]Average of 6 runs. All other data is for single run
[b]Probable large errors because of low yield.

In this case, Zn/Hg amalgam provides the reducing equivalents for activating $O_2$ at the FeP. Although the yields in some cases represent less than one catalyst turnover, the reaction can be continued by adding more amalgam. The FeP or MnP catalyst is required for significant yields of oxidized hexane. In some cases methylviologen is used as a relay molecule, and acetic anhydride is used as an oxygen atom acceptor (as illustrated in Scheme 1). Also, the product yield is sensitive to the amount of water in the acetonitrile solvent, since the sodium sulfate-dried solvent gives almost no oxidation. In addition, acetic acid improves the overall yield and also raises the alcohol/ketone product ratio. Presumably, acetic acid aids in the dioxygen lysis step in the reaction.

EXAMPLE 4

When cyclehexene is the substrate in the dark reaction, the products cyclohexene oxide (1.0 or 20%), 2-cyclohexen-1ol (2.2 or 44%), and 2-cyclohexen-1-one (1.8 or 36%) are observed in the ratios observed in other dioxygen-based systems that mimic the cytochrome $P_{450}$ reaction. Also, when Mn tetraphenyl porphyrin is used as the catalyst, imidazole binding as a fifth ligand acts as a promoter for $P_{450}$ reaction. Both of these results support the contention that the reaction is occurring at the porphyrin catalyst under these solution conditions.

Most importantly, when the FeP catalyst is present in the dark reaction the product ratio is one or less. Therefore, the dark reaction appears to compete favorably with the singlet $O_2$ reaction in the photochemical reaction as shown in Scheme 1. The dark reaction results in the observed lowering in the alcohol/ketone ratio and higher yield measured in the presence of the FeP catalyst. Also, viologen appears not to aid the reaction, since the yield generally remains unchanged or is slightly lowered in its presence (data not shown). This also true of the dark reaction (See Table 2).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for oxidizing hydrocarbons in a catalytic cycle that is driven by a photo-redox cycle that mimics photosynthesis which comprises the steps of:
   providing a solution comprising a metalloporphyrin photosensitizer that generates reducing equivalents for activating oxygen, a biomimetic hydrocarbon-oxidation catalyst, molecular oxygen as the oxidant, a hydrocarbon substrate molecule, a sacrificial electron donor, an acylating agent, and a solvent; and
   irradiating said solution with light in the presence of molecular oxygen.

2. The method as recited in claim 1, wherein the photosensitizer is a tin(IV)- porphyrin.

3. The method as recited in claim 1, wherein the photosensitizer is an antimony(V)-porphyrin.

4. The method as recited in claim 1, wherein the hydrocarbon-oxidation catalyst mimics the cytochrome $P_{450}$ reaction and is a member selected from the group consisting of Fe tetra(pentafluoro-phenyl) porphyrin chloride and iron and manganese porphyrins.

5. The method as recited in claim 1, wherein the oxidant is air.

6. The method as recited in claim 1, wherein the hydrocarbon substrate molecule is a member selected from the group consisting of hexane, hexenes, cyclohexene, ethane, ethylene, butane, butenes, methane and p-xylene.

7. The method as recited in claim 1 wherein the sacrificial electron donor is a member selected from the group consisting of triethanolamine, triethylamine, ethylenediaminetetraacetic acid, ascorbate and mercaptoethanol.

8. The method as recited in claim 1, wherein the solution further comprises an electron relay molecule which is a member selected from the group consisting of heptyviologen, benzyl viologen and methyl viologen and combinations thereof.

9. The method as recited in claim 8, wherein the concentration of the electron relay molecule ranges from $1 \times 10^{-4}$M to 1M.

10. The method as recited in claim 1 wherein the acylating agent is a member selected from the group consisting of acetic anhydride and benzoic anhydride.

11. The method as recited in claim 10, wherein the concentration of the acylating agent ranges from $1 \times 10^{-5}$M to $3 \times 10^{-3}$M.

12. The method as recited in claim 1, wherein the light has a wavelength of 380 nm to 700 nm.

13. The method as recited in claim 1, wherein the reaction temperature ranges from 20° C. to 35° C.

14. The method as recited in claim 1, wherein the concentration the tin(IV)- or antimony(V)-porphyrin ranges from $1 \times 10^{-8}$M to $1 \times 10^{-3}$M.

15. The method as recited in claim 1, wherein the concentration of the sacrificial electron donor ranges from $1 \times 10^{-3}$M to 0.3M.

16. The method as recited in claim 1, wherein the concentration of the hydrocarbon-oxidation catalyst ranges from $1 \times 10^{-8}$M to $1 \times 10^{-3}$M.

17. The method as recited in claim 1, wherein acetonitrile is the solvent.

18. The method as recited in claim 1, wherein the concentration of the hydrocarbon substrate ranges from $3 \times 10^{-3}$M to 1M.

19. The method as recited in claim 1, wherein the reaction is initiated using pulse lasers and the time course of said reaction is followed using time-resolved Raman and absorption spectroscopies.

20. The method as recited in claim 1, wherein the hydrocarbon substrate molecule is an alkane or olefin.

* * * * *